United States Patent

Church et al.

[11] Patent Number: 5,885,611
[45] Date of Patent: Mar. 23, 1999

[54] BANDAGE-FORMING GEL FOR ORAL MUCOSA

[75] Inventors: John A. Church, Princeton Junction; Susan E. Greenfeder, Metuchen, both of N.J.

[73] Assignee: Colgate-Palmolive Company, New York, N.Y.

[21] Appl. No.: 868,661

[22] Filed: Jun. 4, 1997

[51] Int. Cl.$^6$ ...................................................... A61F 13/00
[52] U.S. Cl. .......................... 424/443; 424/435; 424/447; 424/494; 424/495; 514/781
[58] Field of Search ..................................... 424/422, 423, 424/434, 435, 443, 447, 494, 495; 514/781

[56] References Cited

U.S. PATENT DOCUMENTS

| | | | |
|---|---|---|---|
| 5,081,158 | 1/1992 | Pomerantz et al. ...................... | 514/781 |
| 5,166,233 | 11/1992 | Kuroya et al. ............................. | 524/37 |
| 5,236,713 | 8/1993 | Wato et al. ............................... | 424/443 |

*Primary Examiner*—Thurman K. Page
*Assistant Examiner*—Lakshmi Channavajjala
*Attorney, Agent, or Firm*—Paul Shapiro

[57] ABSTRACT

A method of administering an oral bandage to lesions in the oral mucosa is disclosed wherein there is prepared a storage stable topical gel formulation adapted to form an oral bandage adherent to the oral mucosa when applied thereto, the gel containing at least one anesthetic compound, a keratolytic compound, an astringent compound and an ethyl cellulose gelling agent in an amount of at least about 8% by weight and then applying the gel to the area of the oral mucosa experiencing irritation to form an adherent oral bandage.

7 Claims, No Drawings

BANDAGE-FORMING GEL FOR ORAL MUCOSA

BACKGROUND OF THE INVENTION

1. Field of the Invention

This invention relates to a topically applied oral bandage that can be adhered to and is protective of oral mucosa and to a storage stable gel composition providing such bandage.

2. The Prior Art

Aphthous ulcers or oral canker sores are the most common oral lesions afflicting humans. These lesions tend to recur in susceptible patients, often lasting for weeks and are characterized as necrotizing ulcerations of oral mucosal tissue located on soft, non-keratinized mucosa. The lesions are painful, affect nutritional intake, and disrupt oral hygiene. They lead commonly to secondary infections by opportunistic organisms.

Various products are in use for relief of discomfort identified with canker sores and associated lesions such as fever blisters and cold sores, these products forming a protective coating or film about the source of irritation so as to prevent exacerbation of the discomfort caused by normal eating and drinking practices and to allow the lesion to heal naturally. Typically, these products are in the form of ointments and solutions for topical application to the lesions. For the treatment of canker sores, for example, these products have variously employed ingredients such as astringents of which alum and tannic acid are examples, keratolytics such as salicylic acid and anesthetics such as benzocaine.

For example, U.S. Pat. No. 5,081,158 discloses a liquid composition which forms a medicated protective film in situ on oral mucosa, the composition consisting of a medicament dissolved in a solvent such as ethanol, hydroxypropyl cellulose and an agent such as salicylic acid or tannic acid which is disclosed as reacting by esterification with the hydroxypropyl cellulose to form the film. The patent discloses at column 2, lines 27–31, that the formation of the film is specific to hydroxypropyl cellulose and that closely related alkyl or hydroxyalkyl substituted cellulose compounds such as methyl cellulose or hydroxyethyl cellulose are not suitable substitutes for hydroxypropyl cellulose.

SUMMARY OF THE INVENTION

According to the present invention there is provided a method for rapid symptomatic relief of the discomfort associated with lesions of the oral mucosa which method comprises the topical application of a storage stable gel containing an anesthetic compound, an astringent such as tannic acid, a kerolytic compound such as salicylic acid contained in a volatile liquid vehicle such as ethanol and at least 8% by weight of an ethyl cellulose gelling agent, wherein the gel once applied to the oral mucosa, forms upon evaporation of the solvent, an adherent protective film bandage on the afflicted area. The gels of the present invention form an adherent, protective film on the oral mucosa without reliance on chemical reaction as is required with liquid compositions based on hydroxypropyl cellulose.

The oral film bandage formed on lesions in the oral mucosa using the topically applied gel of the present invention exhibits long-lasting adhesion to the oral mucosa, is resistant to removal by saliva flow in the mouth and protects the affected mucosa from worsening of the lesion due to irritation.

DESCRIPTION OF THE PREFERRED EMBODIMENTS

Ethyl cellulose is known to the art and more fully described in the "Encyclopedia of Polymer Science and Engineering", John Wiley, $2^{nd}$ ed. 1985, Vol. 3, p. 254, ff. Ethyl cellulose is soluble in ethanol at a degree of substitution (D. S.) in the range of 2.3 to 2.6.

The amount of ethyl cellulose present in the gel product used in the method of the present invention is from about 8 to about 12% by weight. Concentrations greater than 12% by weight may be used, but such higher concentrations did not materially add to the functionality and stability of the gel product. As will hereinafter be demonstrated, it is critical to the practice of the present invention that the concentration of ethyl cellulose incorporated in the gel formation be at least 8% by weight as such minimum concentration is necessary for satisfactory storage stability of the gel.

Ethyl alcohol is the preferred vehicle for the gel ingredients and preferred amounts range from about 50 to about 60% by weight. Other vehicle materials include purified water in amounts of about 5 to about 10% by and propylene glycol in amounts of about 2 to about 5% by weight.

Benzocaine or benzocaine hydrochloride in amounts of about 10 to about 20% by weight is the preferred anesthetic compound although lidocaine or lidocaine hydrochloride may be substituted for benzocaine or benzocaine hydrochloride. Tannic acid is the preferred astringent compound and is present in the gel formulation at a concentration of about 1 to about 5% by weight. Salicylic acid is the preferred keratolytic agent and is present in the gel formulation at a concentration of about 1 to about 5% by weight.

The gel formulation may also contain pharmaceutically inactive ingredients as for example, a sweetener such as sodium saccharin (0.1–1% by weight) and a flavorant (0.1–1% by weight) such as mint and menthol flavors.

The gel compositions of the present invention are easy to package in conventional containers and as will hereinafter be demonstrated have good stability upon long term storage at ambient and elevated temperatures. Containers known to the pharmaceutical and cosmetic arts as being suitable for the storage and convenient dispensing of gels for topical use may be used to package the gel of the present invention, tubes being preferred as the gel of the present invention is in extrudable form. In tubes, the gel composition of the present invention may be easily transported in an individual's pocket, purse or carrying bag and small quantities may be effectively dispensed for use with little waste and discomfort due to spillage. The gel composition of the present invention is also of pleasant appearance, odor and consistency, all of which promotes and enhances the patient's desire to use the gel composition as needed to relieve pain and discomfort of lesions in the oral mucosa.

The gels of the present invention may be prepared by any conventional process known in the pharmaceutical and cosmetic arts. In accordance with a preferred procedure, a sweetener is dissolved in water to prepare a first phase. A second phase is prepared by mixing antiseptic, flavorant, kerolytic and astringent compounds with alcohol. The first and second phases are then mixed together until a homogenous gel is obtained, all process steps being performed at ambient room temperature (20°–25° C.).

The following example provides a detailed illustration of a gel composition according to the present invention as well as a method of producing the same.

EXAMPLE

A gel formulation adapted for topical application to the oral mucosa to form an oral bandage film to protect lesions formed from further irritation was prepared having the following ingredients:

| Ingredients | Weight % |
| --- | --- |
| Purified water | 6.0 |
| Saccharin sodium | 0.3 |
| Ethyl alcohol (95%) | 57.2 |
| Benzocaine | 15.0 |
| Propylene glycol | 3.0 |
| Tannic acid, USP | 7.0 |
| Salicylic acid USP | 3.0 |
| Mint flavor | 0.5 |
| Ethyl cellulose | 8.0 |

The following procedure was used to prepare the gel formulation:

Fifteen (15) kilograms (kg) of purified water was transferred at 23° C. into a 10 gallon capacity stainless steel kettle equipped with a high speed mixing device. Sodium saccharin USP (0.9 kg) was added to the water and agitation was continued for 15 minutes to assure that the saccharin was dissolved in the water.

Ethyl alcohol 95%, USP (171.6 kg) was transferred into a steam jacketed tank and the temperature maintained at 20°–25° C. Benzocaine (45.0 kg) was added to the ethyl alcohol and then agitated for 10 minutes to insure that the benzocaine was dissolved in the ethyl alcohol. The following ingredients were added to the ethanol solution in the order given and agitation continued for a sufficient time (5–10 minutes) to insure that each ingredient was completely dissolved before adding the next.

Propylene Glycol USP (9.0 kg)

Tannic Acid, USP (21.0 kg)

Salicylic Acid (9.0 kg)

Cool Frost Flavor (1.5 kg)

Ethyl cellulose (24.0 kg)

After complete dissolution of the ingredients added to the steam jacketed tank was achieved, the aqueous saccharin solution from the stainless steel kettle was then added to the ingredients in the steam jacketed tank and the ingredients agitated until complete dissolution was obtained. The resultant composition was a clear amber colored gel having an antiseptic medicinal color and an antiseptic mint taste, a pH of 3.4–3.9 and a specific gravity of 0.8812–0.9740.

For purpose of comparison when the procedure of the Example was repeated except hydroxypropyl methyl cellulose (5.0%) was substituted for ethyl cellulose, the hydroxypropyl methyl cellulose product did not form a homogeneous gel.

The gel composition of the Example was tested for storage stability using an accelerated aging test wherein plastic tubes filled with the gel were maintained at 105° F. for 4 weeks. The results are recorded in the Table below.

For purposes of further comparison, the procedure of the Example was repeated, except that lower concentrations of ethyl cellulose, i.e., 2.5% and 5.0% by weight were used to prepare the gel. The results of these comparative aging tests are also recorded in the Table below.

| Ethyl Cellulose Concentration in Gel (Wt. %) | Aging Period Weeks @ 105° F.) | Appearance of Aged Gel |
| --- | --- | --- |
| 5.0 | 4 | Very thin gel |
| 8.0 | 4 | Thick gel |

It was determined that the gel composition of the Example when topically applied with a cotton swab to the inner lip of human subjects promptly formed a coherent film that was strongly adherent to the mucosa and had an opaque, continuous and occlusive appearance.

To determine the acceptability of the gel of the Example to consumers, sixty-four dentists and oral hygienists at a professional dental meeting were asked to compare the physical properties of the gel product prepared in accordance with the procedure disclosed in the Example against a comparative gel which had been prepared in accordance with the procedure of the Example, except 2.5% hydroxypropyl cellulose was used to prepare the gel instead of ethyl cellulose. The gel prepared in accordance with the Example was preferred by a predominate number of the test participants, that is, 47 of the 64 dental professionals who participated in the evaluation preferred the ethyl cellulose formulated gel product over the hydroxypropyl cellulose formulated gel.

What is claimed:

1. A method of administering an oral bandage to an area of the oral mucosa in need of relief from the discomfort identified with lesions, which method comprises preparing a storage stable topical gel formulation adapted to form an oral bandage adherent to the oral mucosa when applied thereto, the gel containing in a volatile liquid vehicle, at least one anesthetic compound in a therapeutically effective amount for those in need thereof, a keratolytic compound, an astringent compound, and a gelling agent wherein the gelling agent is ethyl cellulose in an amount of at least 8% by weight and then applying the gel to the area of the oral mucosa experiencing irritation to form an adherent oral bandage.

2. The method of claim 1 wherein the anesthetic compound is benzocaine.

3. The method of claim 1 wherein the keratolytic compound is salicylic acid.

4. The method of claim 1 wherein the astringent is tannic acid.

5. The method of claim 1 wherein the volatile liquid vehicle is ethanol.

6. The method of claim 1 wherein the ethyl cellulose is present in an amount of at least about 8% by weight.

7. The method of claim 1 wherein the ethyl cellulose is present in an amount of about 8 to about 12% by weight.

* * * * *